United States Patent [19]

Karpf

[11] Patent Number: 4,955,917
[45] Date of Patent: Sep. 11, 1990

[54] PROSTHETIC ACETABULUM

[75] Inventor: Kurt Karpf, Holderbank, Switzerland

[73] Assignee: Sulzer Brothers Limited, Winterthur, Switzerland

[21] Appl. No.: 333,347

[22] Filed: Apr. 5, 1989

[30] Foreign Application Priority Data

Apr. 11, 1988 [CH] Switzerland .......................... 1322/88

[51] Int. Cl.⁵ .............................................. A61F 2/34
[52] U.S. Cl. ..................................................... 623/22
[58] Field of Search ........................ 623/16, 18, 19, 20, 623/22, 23

[56] References Cited

U.S. PATENT DOCUMENTS

| 3,894,297 | 7/1975 | Mittelmeier et al. | 623/22 |
| 4,650,491 | 3/1987 | Parchinski | 623/22 |
| 4,792,337 | 12/1988 | Muller | 623/22 |
| 4,828,565 | 5/1989 | Duthoit et al. | 623/18 |
| 4,834,759 | 5/1989 | Spotorno et al. | 623/22 |

FOREIGN PATENT DOCUMENTS

| 0242719 | 4/1987 | European Pat. Off. | 623/22 |
| 0270704 | 6/1988 | European Pat. Off. | 128/92 YF |
| 2318459 | 10/1974 | Fed. Rep. of Germany | 623/22 |
| 2349357 | 4/1975 | Fed. Rep. of Germany | 623/22 |
| 2807289 | 8/1979 | Fed. Rep. of Germany . | |
| 2950536 | 7/1981 | Fed. Rep. of Germany . | |
| 3310944 | 10/1984 | Fed. Rep. of Germany | 623/22 |
| 3331191 | 4/1985 | Fed. Rep. of Germany | 623/22 |
| 2478462 | 9/1981 | France | 623/18 |
| 2615726 | 12/1988 | France | 623/18 |
| 1123682 | 11/1984 | U.S.S.R. | 623/22 |

OTHER PUBLICATIONS

Biomedizinische Technik, vol. 32, No. 3, Mar. 1987, Berlin, West Germany, pp. 40-45.

Primary Examiner—David J. Isabella
Attorney, Agent, or Firm—Kenyon & Kenyon

[57] ABSTRACT

The acetabulum has a metal outer shell and a plastic cup within the shell. The outer shell is in the shape of a frustum and at least three plugs extend from about the periphery of the base of the shell for implanting in a hip bone. Each plug has an expandable portion provided with circular toothing and is expandable by a pin which becomes locked in place after expanding the plug within the hip bone.

20 Claims, 3 Drawing Sheets

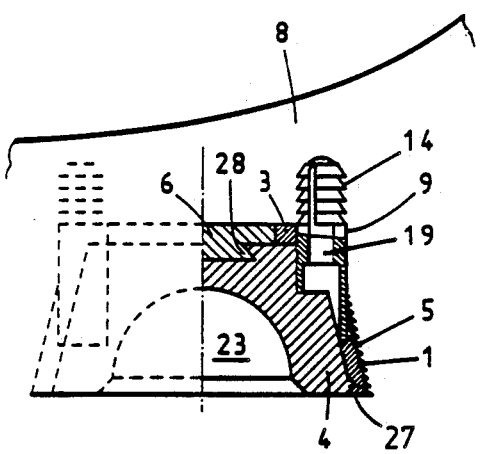
FIG. 5
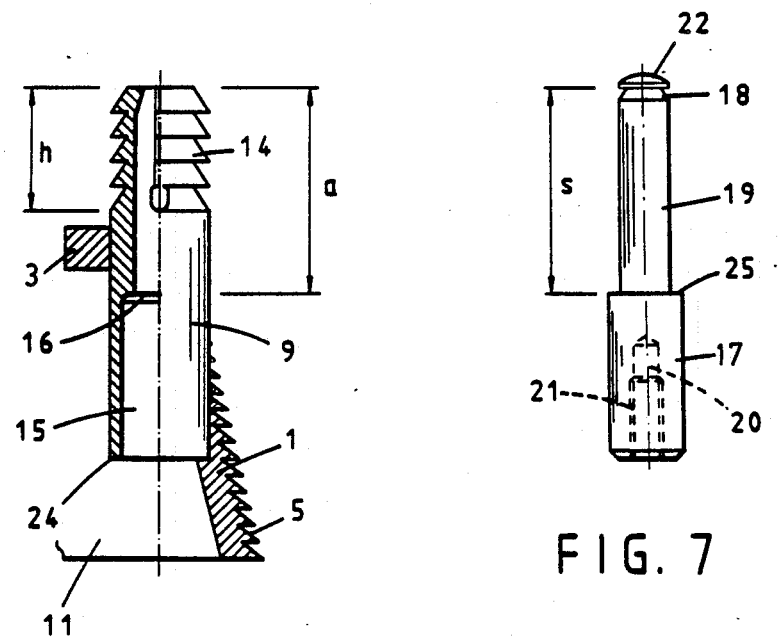
FIG. 6
FIG. 7

PROSTHETIC ACETABULUM

This invention relates to a prosthetic acetabulum. More particularly, this invention relates to a prosthetic acetabulum for cementless fixation in a hip bone.

Heretofore, various constructions have been known for prosthetic acetabula. For example, European Patent 0083708 describes an acetabulum comprising a metal outer shell and a plastic cup or socket having the actual cavity for receiving a femoral head. The outer shell has a shape of a frustum with a base having at least one aperture while the outer surface of the shell has a circular toothing. In addition, the outer shell is slotted so that the shell may expand when the plastic cup or socket is pressed in place to thus expand the outer shell into the hip bone for fixation purposes. Other similar acetabula have a screw thread on the generated surface of the frustum-shaped outer shell which is often of the self-cutting variety to enable the shells to be threaded into a hip bone.

Other types of acetabula have also been known. For example, German OS No. 2807289 describes a hemispherical shaped shell having projecting pins with ribs and recesses for fixation purposes. German OS No. 2950536 describes an acetabulum having a shell with a central recess and screw threads on an outer peripheral surface. Biomedizinische Technik, Vol. 32 No. 3, March 1987, Berlin, West Germany, pages 40–45 describes various types of acetabula made of metal shells and plastic cups.

In the case of re-operations in which a new outer shell has to be fitted into the hip bone, there has frequently been insufficient healthy bone material to ensure a reliable fixation of a prosthetic acetabulum of frustum shape. Further, implantation of the known constructions requires a very high degree of skill on the part of the operating surgeon particularly since the bone hardness varies from patient to patient such that the expansion or threading in of an outer shell is affected.

Accordingly, it is an object of the invention to provide an acetabulum which can be reliably fixed in a pelvis.

It is another object of the invention to provide an acetabulum which can be readily fixed in a pelvis both primarily and secondarily.

It is another object of the invention to be able to manipulate a prosthetic acetabulum during implantation.

It is another object of the invention to ensure that the final seating of a prosthetic acetabulum in an operatively prepared bone is reproducible and uniformly strong.

It is another object of the invention to ensure that the final seating of an acetabulum in a pelvis is affected very little, if at all, by an operating surgeon.

Briefly, the invention provides a prosthetic acetabulum which has a metal outer shell and plastic cup received in the shell and having a cavity to receive a femoral head. The outer shell is of frustum shape having a base and a peripheral wall extending from the base about a central axis.

In addition, at least three plugs extend from the shell at an outer periphery of the base. Each plug is provided with an expandable part which extends from the base on an axis parallel to the central axis and on which a saw tooth circular toothing is provided. The plugs are distributed asymmetrically of the base and each is tangent to a first circle disposed concentrically of the central axis of the shell within the plugs and tangent to a second circle concentric to the central axis and outside the plugs. The first circle is sized with a diameter of at least two-thirds of the inside diameter of the shell at the free edge of the wall while the second circle has a diameter less than the outside diameter of the shell at the free edge of the wall.

A saw tooth toothing is also disposed on the outer surface of the wall of the metal outer shell with a tooth depth of at most one millimeter. This fine toothing and the reduced tooth depth facilitate the invasion of bone substance and not, as is often the case, just of simple connecting tissue, as far as the "root" of the teeth. This characteristic particularly ensures stability of the secondary fixing of the shell in a pelvis. In order to enhance the toothing, a plurality of grooves are disposed radially and circumferentially of the wall of the shell in the toothing.

The three or more plugs on the outer socket periphery are disposed exactly in the direction in which the socket is introduced. The plugs are disposed within the maximum socket diameter but as near the outside as possible to ensure that they are very likely to extend in healthy bone tissue.

The plugs are arranged asymmetrically as referred to the central axis of rotation of the shell to ensure that the outer shell can be introduced only in one predetermined position. This is important particularly in the implantation of sockets or cups having an elevated socket "roof".

Within the contour of the shell, the plugs are plain —i.e., untoothed— or have a rough surface texture while the expandable portions extend beyond the base of the shell. Consequently, the plugs can be accurately guided in correspondingly predrilled bores when the outer shell is introduced into an operatively prepared pelvis, so that introduction of the shell in the "correct" direction is facilitated in a simple way.

In order to eliminate all forms of threading-in of a screw thread whose tightening is a matter of choice depending upon the individual surgeon, the acetabulum has a plurality of pins for expanding the expandable portions of the respective plugs. Each pin is sized to slide into and through a bore of a respective plug in order to expand at least the distal end of the plug. In addition, each pin may be adapted to be hammered in longitudinally of a plug. To this end, each pin has a head at a proximal end bounded by a shoulder. In addition, each pin has a circular recess at a distal end to receive a distal end of a respective plug in locking relation. This serves as a safeguard against the pin slipping out of the plug accidentally. However, when a deliberate removal of a pin is necessary, the proximal end of each pin may be provided with a screw threaded bore adapted to be engaged by an instrument for removal purposes. At this time, the distal end of the pin which may be of mushroom-shape can be torn off.

If the distance between the shoulder and the recess of the pin is equal to the distance between a shoulder in the plug for the pin to bear against and the distal end of the plug, the expanding force for all of the plugs is the same irrespective of the hammering in of the pins by a surgeon.

Conveniently, in order to facilitate backfilling of the outer shell with bone material, the base has a centrally disposed aperture of an area of at least one-third of the area of the base. Direct contact between the pelvis and the plastic cup can be avoided if the aperture is closed by a metal cup.

For improved resilience, the outer shell is provided with slots disposed on meridians and extending from opposite ends of the wall.

In very difficult cases, for example, after repeated re-operations, fixing of the acetabulum can be improved if at least one tab is provided which extends from the wall at the free edge with at least one aperture in the tab.

These and other objects and advantages of the invention will become more apparent from the following detailed description taken in conjunction with the accompanying drawings wherein.

Figure 1:
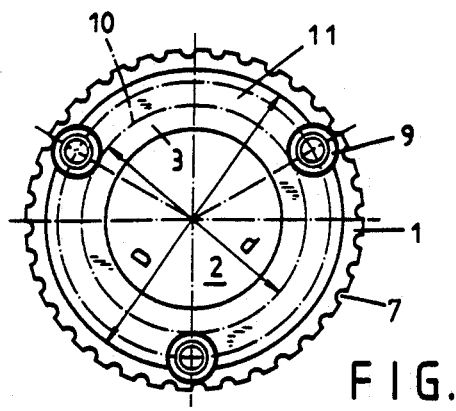
FIG. 1 illustrates a bottom view of the outer shell of an acetabulum constructed in accordance with the invention.
Figure 8:
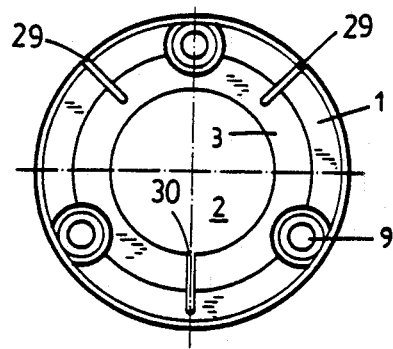
Figure 9:
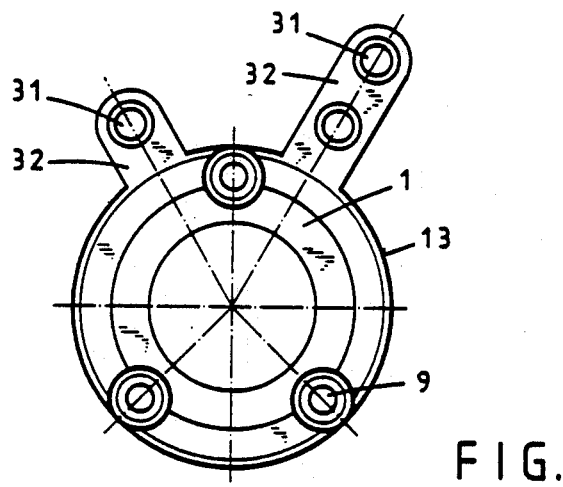
Figure 10:
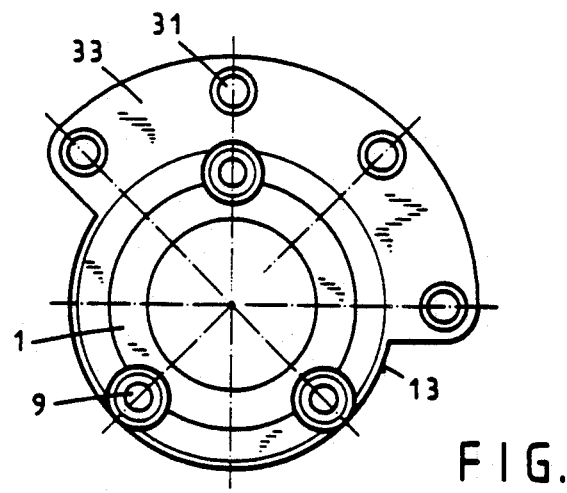

FIG. 5 diagrammatically illustrates an implanted position of the acetabulum of FIG. 1 in a pelvis;

FIG. 6 illustrates an enlarged partial view of the outer shell and a plug in accordance with the invention;

FIG. 7 illustrates a pin used for expanding a plug of the acetabulum;

FIG. 8 illustrates a top view of a modified acetabulum constructed in accordance with the invention;

FIG. 9 illustrates a plan view of a further modified acetabulum having a pair of radially extending tabs in accordance; and FIG. 10 illustrates a plan view of a further modified acetabulum having a single tab of segmental shape in accordance with the invention.

Figure 2:
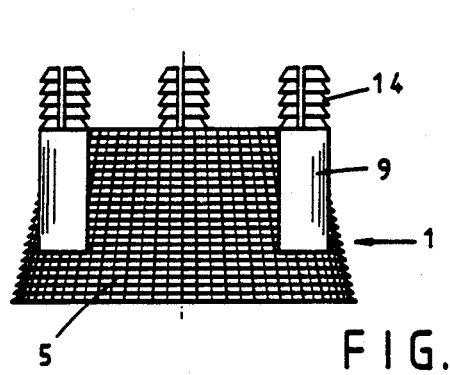
FIG. 2 illustrates a side view of the acetabulum of FIG. 1.
Figure 3:
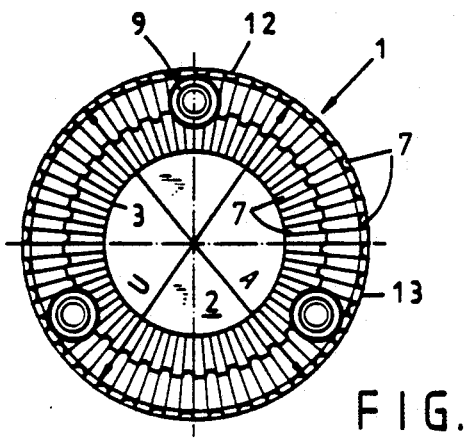
FIG. 3 illustrates a top view of the acetabulum of FIG. 1.

Referring to FIGS. 1 to 3, the prosthetic acetabulum has a metal outer shell 1 of frustum shape having a base or front surface 3 with an aperture 2 disposed on the central axis and a peripheral wall extending from the base 3. As indicated, the aperture 2 is a circular aperture having an area of at least one-third of the area of the base 3, for example, the proportion of the area of the base 3 is approximately 45% of the total area. The aperture 2 enables the implanted outer shell 1 to be backfilled with bone material. The shell is made of any suitable metal such as titanium or a titanium alloy.

Referring to FIG. 5, the acetabulum has a plastic cup 4 received in the shell 1 which is formed with a cavity 23 to receive a femoral head. As indicated, the aperture in the base 3 is closed by a metal cover 6 which is effective to prevent any contact between living tissue and the plastic cup 4.

The frustum shape of the outer shell 1 facilitates centering of the shell at implantation and the centered use of jigs and cutters in the operative preparation of the hip bone.

Referring to FIG. 2, a fine circular saw tooth toothing 5 is disposed on the outer surface of the wall of the shell 1. As illustrated in FIG. 6, the toothing 5 has one inclined flank and one horizontal flank with the tooth depth being at most one millimeter to ensure that spongy bone tissue grows in to the roots of the teeth and not just connective tissue which contributes very little to strong fixing forms between the teeth.

The shell wall may also be provided with grooves 7 which are disposed radially and circumferentially of the wall in the toothing 5 as well as in the base 3. These grooves 7 increase the area of the outer shell 1, thus, of course, improving adhesion between the shell 1 and the hip bone 8 (see FIG. 5).

For a primary fixing of the outer shell 1 in the hip bone 8, at least three metal plugs 9 are distributed asymmetrically of the base 3 relative to the central axis of the shell 1. Thus, the outer shell 1 has only a single defined fitting position. As indicated in FIGS. 1 and 2, the plugs 9 are disposed at the outer periphery of the base 3. In this respect, the plugs 9 are placed as far as possible on the edge of the outer shell 1 so that a large "fixing area" is provided between the plugs 9. This serves to increase the likelihood of the plugs 9 extending into healthy bone tissue.

As indicated in FIG. 1, the plugs 9 are tangent to a first circle 10 disposed concentrically of the central axis of the shell 1 and within the plugs 9 and tangent to a second circle 12 (see FIG. 3) concentric to the central axis and outside the plugs 9. The "thickness" of the plugs 9 is such relative to the size of the outer shell 1 that the diameter d of the first circle 10 is at least two-thirds of the inside of the diameter D of the wall of the shell at the edge 13, that is, the largest inside diameter of an internal cavity 11 of the shell 1. In addition, the second circle 12 has a diameter U (see FIG. 3) which is less than the outside of the diameter A of the wall of the shell 1 at the free edge 13. This dimensioning ensures that the outer boundary of the recess or the like which is to be formed in the bone by surgery can be in the form of a simple frustum and need not be further formed with bulges "extending out" over the edge.

Referring to FIG. 6, each plug 9 has an expandable portion extending from the base 3 of the shell 1 on an axis parallel to the central axis of the shell 1, a cylindrical portion which extends into the shell and a hollow bore 15 which is narrowed at the end projecting over the base 3 on a conical taper. In addition, a shoulder 16 is provided within the plug at a distance a from over the base 3 projecting end of the plug 9. The expandable portion of the plug 9 extends over a height h and is slotted so as to permit expansion of the resulting segments radially outwardly. In addition, a saw tooth circular toothing 14 is provided on the expandable portion. For example, the toothing may have a depth of up to three millimeters. The cylindrical portion of the plug 9 is free of teeth within the shell 1 to facilitate guided introduction of the shell 1 into corresponding bores in the hip bone. Alternatively, the cylindrical portion may be roughened, for example, by sand blasting. As indicated, the lower end 24 of the plug 9 extends to some extent into the cavity 11 of the shell 1.

Figure 4:
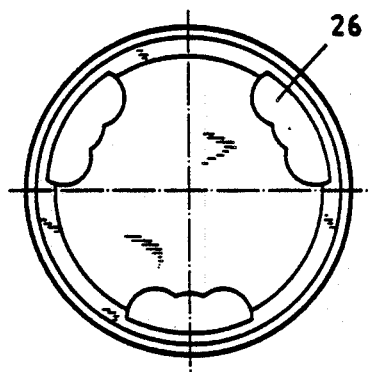
FIG. 4 illustrates a top view of a plastic cup constructed in accordance with the invention.

Referring to FIG. 5, the plastic socket 4 is adapted in shape to fit into the cavity 11 of the outer shell 1. In addition, in order to facilitate some "corrective adjustment" for the asymmetry of the outer shell 1 when cups are used which are not symmetrical about an axis of rotation, for example because of the existence of a socket roof on one side (not shown), the outer contour of the cup 4 has a half-moon-shaped recesses 26 (see FIG. 4) for each plug 9. As indicated, the half-moon-shaped recesses 26 have centers which are offset from one another by 15°.

As indicated in FIG. 5, the cup is retained in the outer shell 1 by a snap fastening 27. In addition, the cover 6 may be secured to the cup 4 by a snap fastening 28.

In order to provide for the expansion of the expandable portions of the plugs 9, a plurality of metal pins 19, only one of which is shown in FIG. 7, are provided. As illustrated, each pin 19 is sized to slide into and through the bore 15 (see FIG. 6) of a respective plug 9 to expand at least the over the base 3 projecting end of the plug 19 by expanding its conical taper. To this end, the pin 19 has a head 17 at a end lying inside of the shell and a circular recess 18 at a end penetrating into the acetabulum to receive the projecting end of the plug 9 in locking relation. In addition, a shoulder 25 is provided between the head 17 and the remainder of the pin 19.

The pin 19 has a length s from the shoulder 25 to the recess 18 which is equal to the distance a between the shoulder 16 in a plug 9 and the projecting end of the plug 9. Thus, after hammering in of a pin, the projecting end of the plug 9 catches in the recess 18 of the pin 19 in locking relation in order to provide a safeguard against the pin 19 accidentally sliding out of the plug 9. In this respect, the pin 19 is hammered into the plug 9 along the axis of the plug without any screwing movement. Another effect of the pins 19 is that the expanding force of the plugs 9 is equal and independent of the force applied by the implanting surgeon.

As shown in FIG. 7, the head 17 in the pin is formed with a blind bore 20 having a screw thread 21 adapted to be engaged by an instrument for deliberate removal of the pin 19. During such deliberate removal of the pin 19, a mushroom-shaped end 22 of the pin 19 is torn off.

Referring to FIG. 8, the resilience of the outer shell 1 for a dynamic resilient radial widening and contraction of a hip bone can be improved if the outer shell 1 is formed with slots 29 30 disposed on meridian walls of the shell. As indicated, the slots 29 extend from one end of the wall while the slots 30 extend from the opposite end of the wall.

Referring to FIG. 9, wherein like reference characters indicates like parts as above, a pair of tabs 32 extend radially from the wall of the shell at the equatorial edge 13 with each tab 32 having one or more apertures therein to enable the acetabulum to be additionally fixed in a hip bone by expanding plugs or bone screws.

Alternatively, as shown in FIG. 10, the acetabulum can be provided with a tab 33 which extends peripherally relative to the outer shell 1. In either case, the tabs 32, 33 can be adapted to be deformed intraoperatively.

After a hip bone has been surgically prepared by a surgeon, for example, withg three bores disposed asymmetrically about a central axis by means of jigs and cutters, the metal shell 1 with the three plugs 9 extending therefrom are fitted into the prepared bone. With the plugs 9 in place, the pins 19 are then fitted into the internal bores 15 of the plugs 9 and hammered in to place. That is, the pins 19 are hammered into such an extent that the distal end of each plug 9 snaps into the circular recess 18 at the end of a pin 19. Next, back filling of the cavity in the hip bone may be performed via the central opening 2 in the shell 1. Thereafter, the plastic cup 4 with the cover 6 snapped thereon is fitted into the shell 1 and snapped in place.

The acetabulum is thus held in place by a primary fixing effected by the expanded portions of the plugs 9. A subsequent secondary fixation is effected by an ingrowth of tissue into the fine toothing 5 about the outer surface of the metal shell 1.

The invention thus provides an acetabulum which is particularly useful in re-operations where the bone substance available for fixing of the acetabulum is often very scarse.

The invention further provides an acetabulum which is able to facilitate the work of the operating surgeon while improving the fixing of the acetabulum in a hip bone, particularly where there is inadequate load-bearing bone substance for implantation.

What is claimed is:

1. A prosthetic acetabulum comprising
   a metal outer shell of frustum shape having a front surface with an aperture disposed on a central axis and a peripheral wall extending from said front surface to an edge;
   a saw tooth toothing disposed on an outer surface of said wall with a tooth depth of at most one millimeter;
   at least three plugs secured to said shell and distributed asymmetrically of said front surface, each said plug having an expandable portion extending from said front surface on an axis parallel to said central axis, said plugs being tangent to a first circle disposed concentrically of said central axis and within said plugs and tangent to a second circle concentric to said central axis and outside said plugs, said first circle having a diameter of at least two-thirds ($\frac{2}{3}$) of an inside diameter of said wall at said edge and said second circle having a diameter less than an outside diameter of said wall at said edge;
   a saw tooth circular toothing on each expandable portion of a respective plug; and
   a plastic cup received in said shell to receive a femoral head.

2. An acetabulum as set forth in claim 1 which further comprises a plurality of grooves in said wall disposed radially and circumferentially of said wall.

3. An acetabulum as set forth in claim 1 wherein said aperture in said front surface has an area at least one-third ($\frac{1}{3}$) of the area of said front surface and which further comprises a metal cover for closing said aperture.

4. An acetabulum as set forth in claim 1 wherein said wall has a plurality of slots disposed on meridians thereof and extending from opposite ends of said wall to impart resilience thereto.

5. An acetabulum as set forth in claim 1 which further comprises at least one tab extending outwardly from said wall at said edge thereof, said tab having at least one aperture therein.

6. An acetabulum as set forth in claim 1 wherein each plug is hollow with a narrowed bore at an upper end opposite said front surface and which further comprises a plurality of pins for expanding said expandable portions of said plugs, each pin being sized to slide into and through said bore of a respective plug to expand said upper end of said respective plug.

7. An acetabulum as set forth in claim 6 wherein each pin has a head, a penetrating portion extending from said head into and through said bore of a respective plug, a circular recess at an end opposite said head to receive a projecting end of said respective plug in locking relation therein and a shoulder between said head and said penetrating portion.

8. An acetabulum as set forth in claim 7 wherein each plug has a shoulder within said bore for mutual abutment of said shoulder of said pin.

9. A prosthetic acetabulum comprising
   a metal outer shell of frustum shape having a front surface and a peripheral wall extending from said front surface about a central axis;

at least three plugs extending from said shell at an outer periphery of said front surface, each said plug having a hollow radially expandable portion extending from said front surface on an axis parallel to said central axis;
a saw tooth circular toothing on an outer surface of said expandable portion of each respective plug; and
a plastic cup received in said shell to receive a femoral head.

10. An acetabulum as set forth in claim 9 wherein said front surface has a centrally disposed aperture of an area of at least one-third (⅓) of the area of said front surface.

11. An acetabulum as set forth in claim 10 which further comprises a metal cover received in said aperture.

12. An acetabulum as set forth in claim 9 wherein said wall has a plurality of slots disposed on meridians thereof and extending from opposite ends of said wall to impart resilience thereto.

13. An acetabulum as set forth in claim 9 which further comprises at least one tab extending outwardly from said wall at said edge thereof, said tab having at least one aperature therein.

14. An acetabulum as set forth in claim 9 wherein each plug is hollow with a narrowed bore at a projecting end from said front surface and which further comprises a plurality of pins for expanding said expandable portions of said plugs, each pin being sized to slide into and through said bore of a respective plug to expand said projecting end of said respective plug.

15. An acetabulum as set forth in claim 9 wherein each pin has a head at an end lying inside of the shell, a circular recess at an end penetrating into the acetabulum said shell to receive the projecting end of said respective plug therein in locking relation and a shoulder between said head and said penetrating end.

16. An acetabulum as set forth in claim 9 wherein said plugs are asymmetrically disposed about said central axis.

17. An acetabulum as set forth in claim 9 which further comprises a sawtooth on said wall with a tooth depth of at most one millimeter.

18. A prosthetic acetabulum comprising
a metal outer shell of frustum shape having a front surface and a peripheral wall extending from said front surface about a central axis;
at least three plugs extending from said shell adjacent an outer periphery of said front surface, each said plug having an upper expandable portion extending from said front surface on an axis parallel to said central axis, a lower cylindrical portion extending into said shell and a hollow bore extending through each of said portions; and
a saw tooth circular toothing on an outer surface of said expandable portion of each respective plug.

19. An acetabulum as set forth in claim 18 wherein at least one plug has a narrowed bore at an end projecting from said front surface and which further comprises at least one pin slidably mounted in said bore of said one plug, said pin being sized to radially expand said expandable portion of said one plug.

20. An acetabulum as set forth in claim 19 wherein said pin has a circular recess at an end penetrating into said one plug to receive a projecting end of said one plug in locking relation.

* * * * *

UNITED STATES PATENT AND TRADEMARK OFFICE
CERTIFICATE OF CORRECTION

PATENT NO. : 4,955,917
DATED : Sept. 11, 1990
INVENTOR(S) : KURT KARPF

It is certified that error appears in the above-identified patent and that said Letters Patent is hereby corrected as shown below:

```
Column 4, line 60 cancel "a"
Column 5, line 4 cancel "the" (first occurrence)
Column 5, line 6 change "a end" to -an end-
Column 5, line 6 change "shell and" to -shell 1 and-
Column 5, line 7 change "a end" to -an end-
Column 5, line 32 change "2930" to -29, 30-
Column 5, line 37 change "indicates" to -indicate-
Column 5, line 47 change "withg" to -with-
Column 5, line 68 change "scarse" to -scarce-
Column 6, line 24 change "(1/3)" to -(2/3)-
```

Signed and Sealed this

Fifth Day of May, 1992

Attest:

DOUGLAS B. COMER

*Attesting Officer*   *Acting Commissioner of Patents and Trademarks*